(12) United States Patent
Stewart (10) Patent No.: US 11,647,934 B2
(45) Date of Patent: May 16, 2023

(54) MONO-LAYER ELECTRODE SENSOR

(71) Applicant: Konan Medical USA, Inc., Irvine, CA (US)

(72) Inventor: Charles Wm. Stewart, Laguna Beach, CA (US)

(73) Assignee: Konan Medical USA, Inc., Irvine, CA (US)

( * ) Notice: Subject to any disclaimer, the term of this patent is extended or adjusted under 35 U.S.C. 154(b) by 1056 days.

(21) Appl. No.: 15/587,721

(22) Filed: May 5, 2017

(65) Prior Publication Data

US 2017/0319093 A1    Nov. 9, 2017

Related U.S. Application Data

(60) Provisional application No. 62/332,660, filed on May 6, 2016.

(51) Int. Cl.
*A61B 5/24* (2021.01)
*A61B 5/282* (2021.01)
(Continued)

(52) U.S. Cl.
CPC ............ *A61B 5/282* (2021.01); *A61B 5/0531* (2013.01); *A61B 5/150206* (2013.01);
(Continued)

(58) Field of Classification Search
CPC ..... A61B 5/04087; A61B 5/0416; A61B 5/04; A61B 5/04085; A61B 5/04001; A61B 5/0531; A61B 5/150206; A61B 5/4893; A61B 5/6833; A61B 5/6832; A61N 2/02; A61N 1/0492
See application file for complete search history.

(56) References Cited

U.S. PATENT DOCUMENTS 4,417,581 A    11/1983  Dawson
4,617,935 A *  10/1986  Cartmell ............ A61B 5/04087
                                                600/392
(Continued)

FOREIGN PATENT DOCUMENTS

JP    2006-003534 Y2    2/1994
WO    2015028589 A1    3/2015

OTHER PUBLICATIONS

Kim, Y., International Application No. PCT/US2017/031231, International Search Report and Written Opinion, dated Jul. 6, 2017, 16 pages.

(Continued)

*Primary Examiner* — Adam Z Minchella
(74) *Attorney, Agent, or Firm* — LaBatt, LLC (57) ABSTRACT

A mono-layer electrode sensor suitable for a multitude of electrophysiology testing applications is disclosed. The electrode sensor can include a mono-layer of conductive film shaped with a soft-form geometry that is modifiable to a targeted size tailored to a patient. The conductive film includes a sensing area that is complementary to a size and morphology of a body structure of the patient. The conductive film can have a connector coupled to the sensor, and the skin adherent side can have a bio-compatible hydrogel coated there over including a non-conductive material formed over the connector portion of the conductive film.

20 Claims, 7 Drawing Sheets

(51) Int. Cl.
*A61B 5/0531* (2021.01)
*A61B 5/15* (2006.01)
*A61B 5/00* (2006.01)
*A61N 2/02* (2006.01)

(52) U.S. Cl.
CPC .............. *A61B 5/24* (2021.01); *A61B 5/4893* (2013.01); *A61N 2/02* (2013.01)

(56) References Cited

U.S. PATENT DOCUMENTS

| | | | |
|---|---|---|---|
| 5,078,139 A * | 1/1992 | Strand | A61B 5/259 |
| | | | 600/393 |
| 5,154,174 A | 10/1992 | Hawlina | |
| 5,297,554 A | 3/1994 | Glynn et al. | |
| 5,772,591 A | 6/1998 | Cram | |
| 7,379,767 B2 * | 5/2008 | Rea | A61B 5/0492 |
| | | | 600/373 |
| 7,496,400 B2 | 2/2009 | Hoskonen et al. | |
| 7,761,131 B2 * | 7/2010 | Copp-Howland | A61K 33/00 |
| | | | 600/391 |
| 9,026,189 B2 | 5/2015 | Garcia et al. | |
| 2007/0293751 A1 * | 12/2007 | Axelgaard | A61B 5/259 |
| | | | 607/152 |
| 2009/0318793 A1 | 12/2009 | Datta et al. | |
| 2012/0165644 A1 * | 6/2012 | Schultz | A61B 5/053 |
| | | | 600/382 |
| 2013/0079618 A1 * | 3/2013 | Sandmore | A61B 5/6839 |
| | | | 600/393 |
| 2013/0197341 A1 * | 8/2013 | Grob | A61N 1/0472 |
| | | | 29/874 |
| 2014/0100432 A1 * | 4/2014 | Golda | A61B 5/04325 |
| | | | 600/301 |
| 2014/0135887 A1 | 5/2014 | Totman et al. | |
| 2014/0142409 A1 | 5/2014 | Garcia et al. | |
| 2014/0323841 A1 * | 10/2014 | Odaka | A61B 5/259 |
| | | | 600/391 |

OTHER PUBLICATIONS

Hawlina, M. et al., "New noncorneal HK-loop electrode for clinical electraretinography," Documenta Ophthalmologica 81, 1992, pp. 253-259.

* cited by examiner

MONO-LAYER ELECTRODE SENSOR

REFERENCE TO RELATED APPLICATIONS

The current application claims the benefit of U.S. Provisional Application No. 62/332,660, which was filed on 6 May 2016, and which is hereby incorporated by reference.

TECHNICAL FIELD

The disclosure relates generally to electrode sensors, and more specifically, to a conductive mono-layer electrode sensor treated with silver/silver chloride having a shape and/or sensing area configured for modification by medical professionals for optimized collection of electrophysiological electrical energy generated from a multitude of anatomical sites.

BACKGROUND ART

Electrode sensors are generally used to collect electrophysiological signals of patients in a wide variety of electrophysiological testing applications. Electroencephalography (EEG), electrooculography (EOG), electromyography (EMG), facial electromyography (fEMG), electroretinography (ERG), and visual electrophysiology (VEP) are a few examples of electrophysiological testing applications in which electrode sensors are used. In these examples of electrophysiological testing applications, the electrode sensors can collect electrophysiological signals produced from a body structure or structures that are the focus of the particular testing application. For example, in EEG, electrode sensors can collect electrical signals from skin locations adjacent to defined brain locations in response to a stimulation. In EOG, electrode sensors can collect electrical signals from skin locations adjacent eye muscles in response to visual stimuli. In EMG, electrode sensors can collect electrical signals from skin locations adjacent skeletal muscles in response to nervous stimulation. In fEMG, electrode sensors can collect electrical signals from skin locations adjacent facial muscles in response to a stimulation. In ERG, electrode sensors can collect electrical signals from conjunctival, corneal, or skin locations adjacent the retina in response to visual stimuli. Additionally, in VEP, electrode sensors can collect electrical signals from skin locations adjacent the visual cortex in response to visual stimuli. In all of these examples, the electrical signals generated from the various body structures are typically in the micro-volt range with some as small as fractions of a micro-volt. Generally, after some averaging and signal processing, the timing and amplitudes of the electrical signals can be used to monitor and assess the function or dysfunction of particular patient body functions.

A number of electrode sensors are currently available that can be used to collect electrophysiological signals for testing applications such as EEG, EOG, EMG, fEMG, ERG, and VEP. A disposal snap skin electrode is one example of an electrode sensor that is used in electrophysiological testing applications. A disposal snap skin electrode is generally round, oval, or rectangular in form, composed typically of non-conductive, non-woven fabric or synthetic material, and is very low cost. However, the disposal snap skin electrode has a geometry that makes it sub-optimal for testing certain body structures targeted in some testing applications. For example, the disposal snap skin electrode is not well suited for obtaining electrophysiological signals from the lower eye lid for ERG testing, the eye adnexa for EOG testing, or longer facial muscles for fEMG. The geometry of the disposal snap skin electrode is also not well suited for use in EMG and ECG applications. A second example is that the disposal snap skin electrode has a sensing area that is not advantageous for testing certain body structures targeted in EOG, EMG, fEMG, ERG, EEG, and VEP. For example, the disposal snap skin electrode can have a central round sensor of only approximately 10 mm$^2$ surrounded by a much larger non-sensor fabric supportive area for skin adherence. This type of sensing area configuration for an electrode sensor does not perform well in EOG, EMG, fEMG, ERG, and VEP testing applications due to the smaller-sized sensing area.

A contact lens encapsulated electrode is one example of an electrode sensor that can be used to test the retina in ERG. In particular, the contact lens encapsulated electrode can be placed on the eye's cornea with a cable extending off of the lens and out of the eye and lid area. In this manner, the contact lens encapsulated electrode is physically close to the source of retinal ERG energy, i.e., it is not insulated by the eyelid from ERG energy. However, the contact lens encapsulated electrode may not be tolerated well by a patient, either physically or emotionally with lead wires extending out from the eye. Also, this contact lens encapsulated electrode generally has a high per unit cost due to a complex encapsulated manufacturing method that typically relies on precious metals, thereby making them unsuitable for use as a disposable electrode sensor. Furthermore, this contact lens encapsulated electrode has a circular sensing area that is not optimal for testing other body structures in the eye. For example, the contact lens encapsulated electrode sensing area typically traces a diameter of about 10 mm, but has an effective sensing area of only approximately 15 mm$^2$ which may not be optimum for ERG nor have any practical application for other electrophysiological testing such as EEG, EOG, EMG, fEMG, and VEP.

A precious metal thread or "loop" electrode is another example of an electrode sensor that can be used to test the retina in ERG. The precious metal thread electrode is typically physician hand-shaped to hang from the eye lid with a linear section of the thread placed under the eyelid entrapped between the eyelid and eye's conjunctiva. The precious metal thread is traced along a linear path in the lid fornix. In this manner, the precious metal thread electrode occupies only a very small surface area due to the diameter of the thread, but effectively eliminates the insulating characteristics of the eyelid due to the proximity to the retina for collection of an ERG signal. However, the precious metal thread electrode is not well suited for electrophysiological testing applications such as EEG, EOG, EMG, fEMG, and VEP. Furthermore, the loop electrode may not be tolerated well by a patient, either physically or emotionally with lead wires extending out from the eye and may require topic anesthesia for patient tolerance of the device. In addition, the precious metal thread electrode has a high per unit cost which makes them unsuitable for use as a disposable electrode sensor.

A silver-impregnated nylon-thread electrode is another example of an electrode sensor that can be used to test the retina in ERG. In one example, the silver-impregnated nylon-thread electrode can include approximately 6.5 cm of thread affixed to two self-adhesive pads which attach to the inner and outer eye canthus for clinical ERG registrations. An extension cable is typically used to connect the silver-impregnated nylon-thread electrode to a recording instrument. The silver-impregnated nylon-thread electrode does not have any practical application for other electrophysiological testing such as EEG, EOG, EMG, fEMG, and VEP.

Additionally, the silver-impregnated nylon-thread electrode may not be tolerated well by a patient, either physically or emotionally with lead wires extending out from the eye and may require topic anesthesia for patient tolerance of the device.

Another electrode sensor only described for use with ERG applications involves a multi-layered, multi-sectioned electrode having a first section that has a non-conductive base scaffolding layer with a conductive material deposited thereon that includes a sensing area. This section of the multi-layered electrode sensor further includes an adhesive and medical tape formed over the conductive material. The conductive material is attached to a connector that runs through a narrower, non-adhesive intermediate area that is not attached to the skin that forms a second section of the multi-layered electrode sensor. The connector is coupled to a third section of the sensor that also is a non-adhesive and not attached to the skin. At this third section, the conductive material can attach to a terminal.

This multi-layered electrode sensor has its limitations in ERG applications. For example, the multi-layered electrode sensor has a substantially small square sensing area of approximately 35 mm$^2$ that necessitates the use of a skilled technician to ensure placement of the sensing area that is defined to be directly below and in line with the eye's pupil. Even with the aid of a technician, placement of this electrode sensor can be difficult. As a result, the multi-layered electrode sensor is configured with a visible indication or index marking that the technician uses as an aid in positioning the sensing area to the desired location. The small sensing area of the multi-layered electrode sensor may not be optimized for the size of the targeted organ, the retina, that has a lower-lid adjacent area of approximately 70 mm$^2$. Furthermore, both the small, generally square, sensor area with the long, linear, non-customizable, non-sensing substrate multi-layered geometry makes it unsuitable for use with other electrophysiological testing applications such as EEG, EOG, EMG, fEMG, and VEP. In particular, the multi-layered electrode sensor has an outermost layer that is both supportive and insulating in that it covers the full external electrode surface. In addition, there is an additional insulating layer on an opposite side of the electrode sensor that covers approximately 90% of the non-sensing areas of the skin-side of the electrode, leaving only about 10% exposed for detecting weak electrical signals, which makes it difficult for this type of sensor electrode to collect an adequate amount of electrical signals, be optimally positioned at the defined position directly under the eye's pupil, or be optimally positioned due to the length for monitoring and diagnosing a patient using any of these other electrophysiological testing applications.

The multi-layered electrode sensor also has a high lateral rigidity that can affect conformance to lax or wrinkled skin that is common to the targeted sensing site. This can make the electrode sensor's adherence to lid rhytides inconsistent uncomfortable for the patient undergoing the ERG test. Additionally, the overall structure of the multi-layered electrode sensor, with the multiple layers, contributes to a high per-unit cost of manufacture, which can detract from its desirability for use as a disposable electrode sensor. In addition, the multi-layered electrode sensor relies on non-industry standard, proprietary, micro-connectors that are atypical for use in many of the aforementioned electrophysiological testing applications. Furthermore, the geometry of the multi-layered electrode sensor, which is used only below the lower-lid for ERG signal recording, does not make it conducive for application to other anatomical sides for recording other body structures that are tested in applications such as EEG, EOG, EMG, fEMG, and VEP.

SUMMARY OF THE INVENTION

This summary of the invention introduces a selection of certain concepts in a brief form that are further described below in the detailed description of the invention. It is not intended to exclusively identify key features or essential features of the claimed subject matter set forth in the claims, nor is it intended as an aid in determining the scope of the claimed subject matter.

Aspects of the present invention are directed to an electrode sensor having high flexibility and conductivity that is suitable for a multitude of electrophysiological testing applications that can include electroencephalography (EEG), electrooculography (EOG), electromyography (EMG), facial electromyography (fEMG), electroretinography (ERG), electrocardiogram (ECG) and visual electrophysiology (VEP). In one embodiment, the electrode sensor can be formed as a large curvilinear-shaped sensing area that is configured for placement at a variety of anatomical sites in order to collect electrophysiological electrical signals that can be generated from a number of different body structures. For example, the curvilinear-shaped electrode sensor can collect electrophysiological electrical energy produced from face, head and eye originated tissues and muscles. In one embodiment, the curvilinear-shaped electrode sensor can include a simplified construction of a mono-layer of carbon conductive film that is enhanced with a conductive treatment, such as for example, a printing-impregnated Ag/AgCl conductive treatment. An offset connector can attach directly to the electrode sensor, with only the connector and a perimeter of the connector covered by a non-conductive insulating material.

The entire area of the skin-side of the electrode sensor can be covered with a bio-compatible hydrogel, such as for example, an Ag/AgCl hydrogel. In another embodiment, the mono-layered electrode sensor can be shaped with a rectangular geometry. The shape and sensing area size of both the curvilinear-shaped electrode sensor and the rectangular-shaped electrode sensor can be configured for collection of small microvolt electrical signals, including weak signals that are fractions of microvolts, that can be generated from a multitude of anatomical sites, for example, the head, the face and the eyelids. In addition, both the curvilinear-shaped electrode sensor and the rectangular-shaped electrode sensor can be modifiable or customized by a physician or medical staff by trimming the conductive film area with scissors or other common sharps to a targeted size or shape that is tailored to the patient or certain body structure of the patient that is subject of an electrophysiological testing application. For example, the rectangular-shaped electrode sensor can be modified to have a single edge curve or a concave curved edge that substantially matches morphometrically with an eyelid of an infant. Common disposable electrodes customarily have a sensing area constrained to a non-modifiable hard metal or other conductive material surrounded by a non-conductive film or cloth carrier.

A first aspect of the invention provides an electrode sensor, comprising: a mono-layer of conductive film that is continuously conductive from a first end to an opposing second end, the conductive film having a first side adapted for placement facing an anatomical site of a patient and a second side, opposing the first side, the conductive film shaped with a soft-form geometry that is modifiable to a targeted size that is tailored to the patient, wherein the conductive film provides a sensing area that is complementary to a size and morphology of a body structure of the patient that is proximate the anatomical site, the sensing area adapted to collect electrical signal representations of electrophysiological electrical energy generated from the body structure and generate signal representations thereof, and a connector coupled to the conductive film for connection to the electrophysiological device.

A second aspect of the invention provides an electrode sensor, comprising: a mono-layer of conductive film that is continuously conductive from a first end to an opposing second end, the conductive film having a first side adapted for placement facing an anatomical site of a patient and a second side, opposing the first side, the conductive film shaped with a curvilinear geometry that is modifiable to a targeted size that is tailored to the patient, wherein the conductive film provides a large sensing area that is complementary to a size and morphology of a body structure of the patient that is proximate the anatomical site, the large sensing area adapted to collect electrical signal representations of electrophysiological electrical energy generated from the body structure and generate signal representations thereof; a connector coupled to the conductive film proximate the first end, wherein the connector includes a base portion formed on the first side and the second side of the conductive film and a projection element supported by the base portion that extends outward through the second side of the conductive film; a non-conductive material formed on only a portion of the first side of the conductive film, wherein the non-conductive material extends along the first side of the conductive film beyond a perimeter of the connector, with one end of the non-conductive material being in vertical alignment with the first end of the conductive film and another opposing end of the non-conductive material extending along the first side of the conductive film; and a hydrogel coated over the first side of the conductive film and the non-conductive material.

A third aspect of the invention provides an electrode sensor for detecting electrophysiological electrical energy generated from an anatomical site of a patient, comprising: a mono-layer of conductive film having a first side adapted for placement facing the anatomical site of the patient and a second side, opposing the first side, the conductive film shaped with a rectangular geometry that is modifiable to a targeted shape that is tailored to the patient, the targeted shape including at least one edge of the rectangular geometry having one of a single edge curve or a concave curved edge, wherein the conductive film includes a sensing area that substantially matches morphometrically with a body structure of the patient that is proximate the anatomical site, the sensing area adapted to collect electrical signal representations of electrophysiological electrical energy generated from the body structure and generate signal representations thereof; a connector coupled to the conductive film, wherein the connector includes a base portion formed on the first side and the second side of the conductive film and a projection element supported by the base portion that extends outward through the second side of the conductive film; a non-conductive material formed on only a portion of the first side of the conductive film corresponding to the connector; and a hydrogel coated over the first side of the conductive film and the non-conductive material.

A fourth aspect of the invention provides a system, comprising: at least one electrode sensor including a mono-layer of conductive film that is continuously conductive from a first end to an opposing second end, the conductive film having a first side adapted for placement facing an anatomical site of a patient and a second side, opposing the first side, the conductive film shaped with a soft-form geometry that is modifiable to a targeted size that is tailored to the patient, wherein the conductive film includes a large sensing area that is complementary to a size and morphology of a body structure of the patient that is proximate the anatomical site, the sensing area adapted to collect electrical signal representations of electrophysiological electrical energy generated from the body structure and generate signal representations thereof, and a connector coupled to the conductive film; and an electrophysiological device, operatively coupled to the second side of the electrode sensor to monitor the signal representations of the electrophysiological electrical energy generated therefrom, the electrophysiological device including a signal processing unit to process the signal representations and a control unit to monitor the patient and perform a physiological analysis as a function of the signal representations. In this aspect of the invention, the electrode sensor and the electrophysiological device can be used for an electrophysiological application selected from the group consisting of electroencephalography (EEG), electrooculography (EOG), electromyography (EMG), facial electromyography (fEMG), electroretinography (ERG), and visual electrophysiology (VEP).

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the present invention are directed to an electrode sensor having high flexibility and conductivity that is suitable for a multitude of electrophysiological testing applications that can include electroencephalography (EEG), electrooculography (EOG), electromyography (EMG), facial electromyography (fEMG), electroretinography (ERG), electrocardiogram (ECG) and visual electrophysiology (VEP). In one embodiment, the electrode sensor can be formed as a large curvilinear-shaped sensing area that is configured for placement at a variety of anatomical sites in order to collect electrophysiological signals generated from a number of different body structures. For example, the curvilinear-shaped electrode sensor can collect electrophysiological electrical energy produced from face, head and eye originated tissues and muscles. In one embodiment, the curvilinear-shaped electrode sensor can include a simplified construction of a mono-layer of carbon conductive film that is enhanced with a conductive treatment such as for example, a printing-impregnated Ag/AgCl conductive treatment. An offset connector can attach directly to the electrode sensor, with only the connector and a perimeter of the connector covered by a non-conductive insulating material.

The entire area of the skin-side of the electrode sensor can be covered with a bio-compatible hydrogel such as, for example, an Ag/AgCl hydrogel. In an embodiment, the hydrogel can be formulated for: adherence to delicate skin; release characteristics for comfortable removal from skin after use; low resistivity for electrical signal transmission; and/or the like. In another embodiment, the mono-layered electrode sensor can be shaped with a rectangular shape. The shape and sensing area size of both the curvilinear-shaped electrode sensor and the rectangular-shaped electrode sensor can be configured for collection of small microvolt electrical signals, including weak signals that are fractions of microvolts, that can be generated from a multitude of anatomical sites of the head, face and eyes. In addition, both the curvilinear-shaped electrode sensor and the rectangular-shaped electrode sensor can be modifiable or customized by the physician or medical staff (collectively referred to as "medical personnel") by trimming the conductive film area with scissors or other commons sharps to a targeted size or shape that is tailored to the patient or certain body structure of the patient that is subject of an electrophysiological testing application. For example, the rectangular-shaped electrode sensor can be modified to have a single edge curve or a concave curved edge that substantially matches morphometrically with an eye of an infant. This provides an advantage over common disposable electrodes that customarily have a sensing area constrained to a non-modifiable hard metal or other conductive material surrounded by a non-conductive film or cloth carrier.

Figure 1:
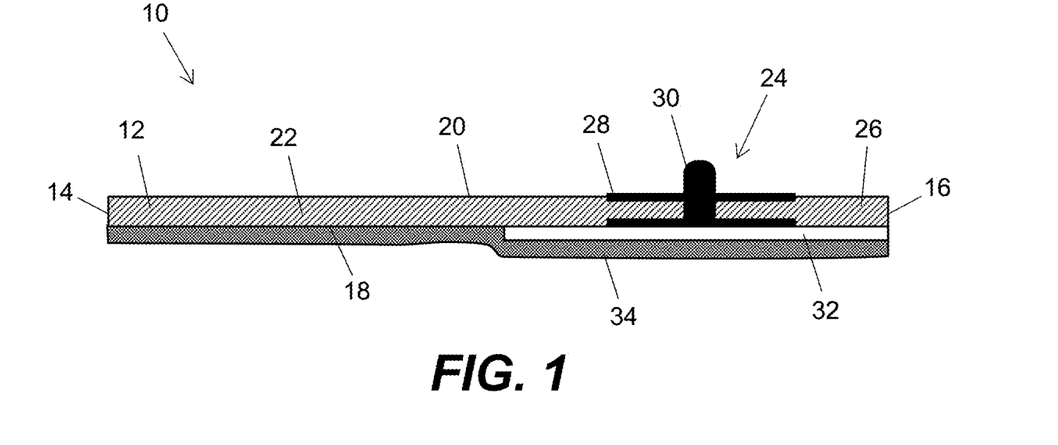
FIG. 1 is a cross-sectional view of an electrode sensor according to an embodiment.

Referring now to the drawings, FIG. 1 is a cross-sectional view of an electrode sensor 10 according to an embodiment of the present invention. As shown in FIG. 1, the electrode sensor 10 can include a mono-layer of conductive film 12 that is continuously conductive from a first end 14 to an opposing second end 16. The conductive film 12 has a first side 18 adapted for placement facing an anatomical site of a patient. In this manner, the first side 18 of the conductive film 12 takes the form of a skin adherent. The conductive film 12 further includes a second side 20, opposing the first side, which can be adapted to connect with an electrophysiological device. The conductive film 12 can be shaped with a soft-form geometry that is modifiable to a targeted size tailored to the patient and/or application. As used herein, a soft-form geometry means the morphology of the electrode sensor 10 is constructed to generally eliminate sharp edges, hard surfaces, and rigid structure so as to minimize any patient discomfort or awareness of the sensor.

The conductive film 12 includes a sensing area 22 that is complementary to a size, location and morphology of a body structure of the patient that is proximate the anatomical site in which the electrode sensor 10 is to be placed. As used herein, a sensing area that is complementary to a size, location and morphology of a body structure means that the electrical energy receiving area of the sensing area 22 has a shape and surface area that generally match the shape and surface area of the anatomical structure that is producing the electrical energy or provides a curved, generally equidistant receiver from a body part or organ that is producing electrical energy. In operation, the sensing area 22 can collect electrical signal representations of electrophysiological electrical energy generated from the body structure upon electrical stimulation and generate signal representations thereof, which can be processed by a computer system that can be used as part of the testing application.

The sensing area 22 can include a large sensing area that enhances a capability of the electrode sensor 10 to collect minute electrical signals ranging from microvolts to fractions of microvolt electrical energy emitted from a variety of body structures that can include, but are not limited to, face, eye and head originated tissues and organs. A non-exhaustive list of face, eye and head originated tissues and organs that the large sensing area 22 of the electrode sensor 10 is well suited for obtaining electrophysiological electrical energy produced from face, eye and head originated tissues and organs can include eye muscles, facial muscles, the retina, the iris, and the like. In an embodiment, the large sensing area 22 can enable the electrode sensor 10 to capture a larger signal sampling that includes very weak, microvolt or fractional microvolt electrical energy emitting tissue and organ areas in comparison to electrode sensors that utilize mini-sensing areas in ERG applications.

As used herein, a large sensing area means a sensing area of at least about 70 mm$^2$. In a more particular embodiment, the large sensing area is in a range of about 70 mm$^2$ to about 600 mm$^2$. In a still more particular embodiment, the large sensing area 22 can include a sensing area that ranges from about 200 mm$^2$ to about 400 mm$^2$. In an illustrative embodiment, the large sensing area encompasses about 25% to about 50% of a total surface area occupied by the conductive film 12. In this manner, the sensing area 22 of the electrode sensor 10 can be used to provide at least partial circumference coverage of a body structure. Depending on the size, location and morphology of the body structure, the sensing area 22 of the electrode sensor 10 can be used to provide complete coverage of the size, the location and the morphology of the body structure. In either embodiment, the sensing area 22 of the electrode sensor 10 can generally complement the size and shape of a targeted organ or tissue to capture radiated energy from the relevant body structure in the form of very low amplitude electrical signals which are typically in the fractions to several microvolt range.

In addition to providing a large sensing area that increases collection of microvolt or fractional microvolt electrical energy produced from a variety of different body structures, the sensing area 22 of the electrode sensor 10 can have further advantages over electrode sensors that utilize mini-area sensing areas. For example, having a large sensing area obviates the need for a visible indicator on the outer surface of the electrode sensor that is used by medical professionals as an aid to enable precise placement of the sensor, such as directly under the eye's pupil. As a result, application complexity of the electrode sensor 10 is reduced in comparison to that of electrode sensors that utilize mini-sensing areas.

In one embodiment, the mono-layer of conductive film 12 can include a thin, carbon conductive film impregnated with a silver conductive treatment. For example, the carbon conductive film can be enhanced with a printing-impregnated silver conductive treatment that includes Ag/AgCl. Other examples of carbon conductive film that are suitable for use as the conductive film 12 can include, but are not limited to carbon based fabrics that may also be impregnated with silver conductive treatments. In embodiment, the carbon conductive film 12 can have a thickness that ranges from about (+/−20%) 1 mil to about 5 mils. This thickness enables the electrode sensor 10 to be highly flexible and adaptive to take the form of the skin in which it is to be applied. In addition, the conductive film 12 in the electrode sensor 10 can have the added benefit in a reduced device complexity and costs by using a conductive carbon film mono-layer structure.

As shown in FIG. 1, the electrode sensor 10 can further include a connector 24 coupled to the conductive film 12 outside of the sensing area 22 in a non-sensing area 26. In one embodiment, the connector 24 can include a base portion 28 formed on the conductive film 12 and a projection element 30 supported by the base portion 28 that extends outward through the conductive film 12 and the base portion on the second side 20 of the conductive film 12 in order to connect with an electrophysiological device. In this manner, the connector 24 can be inclusive with the conductive film 12 and form a full perimeter connection to an industry standard connector to the electrophysiological device such as a terminal connector. In one embodiment, the connector 24 can include an offset connector. It is understood, that other types of connectors that are commonly used with electrophysiology devices and testing systems can be used with the electrode sensor 10. Thus, the various embodiments of the present invention are not meant to be limited to use with an offset connector. For example, a stud and eyelet snap or alligator clip connectors could be used with the various electrode sensors described herein.

The electrode sensor 10 can further include a non-conductive material 32 formed on only a portion of the first side 18 of the conductive film 12 that is applied to the skin of a patient. In one embodiment, the non-conductive material 32 extends along the first side 18 of the conductive film 12 beyond a perimeter of the connector 24. As shown in FIG. 1, one end of the non-conductive material 32 can be in vertical alignment with the second end 16 of the conductive film 12 and another opposing end that extends along the first side 18 of the conductive film 12 to about a mid-region thereof. In this manner, the non-conductive material 32 can serve as an isolation zone in the electrode sensor 10 by surrounding the connector 24. In this isolation zone, the conductive film 12 does not function as a sensing area as the non-conductive material 32 insulates in this particular region of the conductive film.

The non-conductive material 32 can include a non-conductive film, layer or fabric. The non-conductive material 32 can include an insulating material or a dielectric material. Examples of non-conductive material that are suitable for use with the various electrode sensors of the present invention can include, but are not limited to, non-woven fabrics of natural or synthetic materials, or bio-compatible polymers.

FIG. 1 shows that the electrode sensor 10 can further include a bio-compatible hydrogel 34 coated over the first side 18 of the conductive film 12 and the non-conductive material 32 that is applied to the dermal surface or skin of a patient. The bio-compatible hydrogel 34 enables the electrode sensor 10 to be applied to multiple dermal locations and enhances conformance and comfort of the electrode sensor 10 to a targeted skin area which may include wrinkled or non-flat skin. In one embodiment, the bio-compatible hydrogel 34 can include an Ag/AgCl hydrogel. It is understood, that other types of hydrogels that are commonly used with electrophysiology devices and testing systems can be used with the electrode sensor 10, and thus, the various embodiments of the present invention are not meant to be limited to use with an Ag/AgCl hydrogel.

Combining the mono-layer of conductive film 12 with the non-conductive material 32 and the hydrogel 34 can enable the electrode sensor 10 to have a highly flexible construction that imparts comfort to a patient when applied to a specific anatomical site regardless if there is wrinkled or non-flat skin. The more rigid, multi-ply architectures used with conventional electrode sensors are not well-suited for application to a multiple of anatomical sites in comparison to the electrode sensors of the various embodiments described herein which afford a smooth and comfortable application to multiple dermal locations. Regardless, it is understood that embodiments of the electrode sensors described herein can be fabricated with a more rigid and/or multi-ply architecture.

In addition, the configuration of the mono-layer of conductive film 12 with the non-conductive material 32 and the hydrogel 34 in the embodiments described herein can allow the electrode sensor 10 to be minimally invasive, and enables placement of the electrode sensing area close to the source(s) of the electrical energy generating anatomy with a minimum of other tissues acting as insulators and adding noise to the recorded electrical energy by the electrode sensor 10. Furthermore, the configuration of the mono-layer of conductive film 12 with the non-conductive material 32 and the hydrogel 34 can permit the manufacture of the electrode sensor 10 to be based on a minimalist fabrication that uses low-cost materials that is not reliant on either significant quantities of precious metals or complex multi-layers each with disparate features. In addition, this minimalist fabrication obviates multi-zonal fabrication techniques to hold small sensing areas as is the case with many conventional electrode sensors. Furthermore, these conventional electrode sensors typically rely on secondary conductors to transmit electrical signals from the sensing areas to a connector area. This allows the electrode sensor 10 to have reduced manufacturing costs that allows the sensor to be used as a single-use disposable electrode sensor. However, it is understood that embodiments of the electrode sensor 10 can be implemented without attaining one or more of these benefits.

The thin and highly flexible electrode sensor 10 that is attained with the non-conductive material 32 and the hydrogel 34, makes the sensor 10 modifiable to obtain a size and shape that is targeted specifically for a certain patient. In this manner, the electrode sensor 10 can be customized for a fitting to individual facial features or targeted physiology. For example, an infant may have different sizes and shapes of body structures than an adult, making it desirable to have a customized fitted electrode sensor. In this case, a portion of the electrode sensor 10 can be cut or trimmed to a size and/or shape that is tailored to the infant. The electrode sensor 10 can be cut or trimmed in a number of different ways. For example, scissors, a knife, a scalpel or the like can be used to cut the electrode sensor. In one embodiment, the electrode sensor 10 can be prefabricated with one or more score lines to facilitate cutting the sensor 10 at predetermined locations. A scored line can be located at a location representative of a sensing area size that is expected to fit different patients of different sizes and shapes and/or different anatomical sites.

Figure 2A:
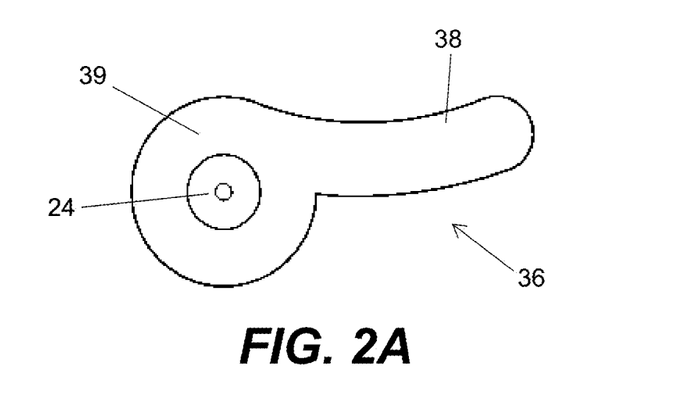
FIGS. 2A-2B are top and bottom views of an electrode sensor having the structure depicted in FIG. 1 with a curvilinear shape according to an embodiment.
Figure 2B:
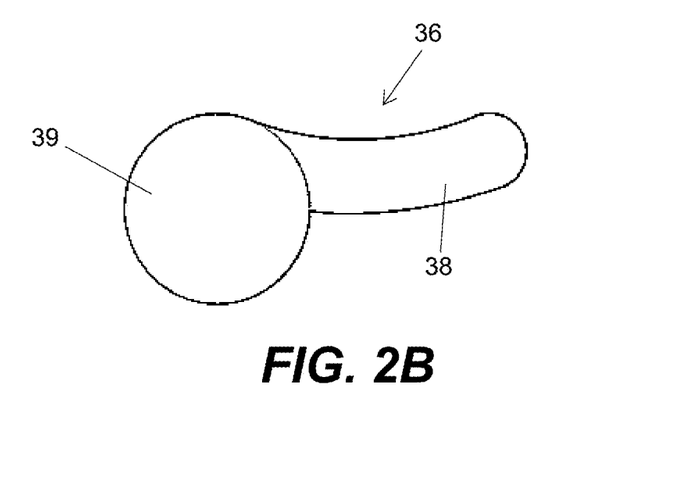

In one embodiment, the soft-form geometry of the conductive film 12 of the electrode sensor 10 can include a curvilinear shape. FIGS. 2A-2B show top and bottom views, respectively, of an electrode sensor 36 having a curvilinear shape according to an embodiment. Like the electrode sensor 10, the electrode sensor 36 of FIGS. 2A-2B can have a sensing area 38 and a connector 24 in a non-sensing area 39 outside of the sensing area 38. The sensing area 38 can include a large sensing area configured for collection of electrical energy signals produced from a variety of anatomical sites. The connector 24 can include an offset connector or one of the other types of connectors that are commonly used with electrophysiological devices. In one embodiment, a sensing area 38 of the electrode sensor 36 can include a curvilinear and organic form that is similar to a comma with a reversed curve. The conductive curvilinear shape may occupy a surface area of approximately 300 mm$^2$+/−30%, with the curve approximating the circumference of a 75 mm diameter circle, +/−20%. A notable aspect of the surface area size, is that medical personnel can cut the shape to customize the area to more accurately cover a targeted energy producing structure, such as for infants that have small physical attributes in comparison to adults.

Shaping the large sensing area 38 of the electrode sensor in a curvilinear and organic form similar to a comma with a reversed curve is generally consistent with or complementary to the size, location, and morphology of a plurality of targeted physical locations or anatomical sites of a patient that may radiate small amounts of electrical energy upon stimulation. In this manner, the curvilinear-shaped electrode sensor 36 can overlay certain anatomical sites to provide generally complete coverage of some body structures. Alternatively, in some implementations, the curvilinear-shaped electrode sensor can be placed equidistant from a targeted anatomical site and still collect radiating electrical energy from a particular body structure due to the geometry and the large sensing area of the sensor. In another implementation, the curvilinear-shaped electrode sensor can be placed about a targeted anatomical site to provide at least partial circumference coverage of the body structure.

It is understood that the relative location of the non-sensing area 39 to the large sensing area 38 is only illustrative. To this extent, in an embodiment, an electrode sensor 36 can be fabricated with the non-sensing area 39 located on an opposite side of the large sensing area 38 (e.g., on the right side of the large sensing area 38 shown in FIGS. 2A and 2B). In this case, the electrode sensor can comprise a mirror image of the electrode sensor 36. Each alternative configuration may be more suitable for placement in a particular location as shown herein. Similarly, embodiments also can include the non-sensing area 39 centrally located with respect to the large sensing area 38. In this case, the non-sensing area 39 can be located on the outer curve side (e.g., the bottom side of the electrode sensor 36 shown in FIGS. 2A and 2B) of the large sensing area 38.

As a result, the curvilinear-shaped electrode sensor 36 can be placed on a variety of positions and sites of a patient. Facial features, including, but not limited to, brows, temples, forehead, cheeks and the like, are well suited for having the electrode sensor 36 placed thereon. A non-exhaustive list of other features that are suitable for placing the electrode sensors 36 can include directly on either upper or lower eyelids, the contour of non-planar areas such as rhytides, concave and convex skin areas, and other facial, head, or periorbital positions in which the electrode sensor 36 can be dermally applied. The flexibility of positioning and size matching associated with the curvilinear-shaped sensor electrode 36 facilitates morphometrically matching with body structures at or near certain targeted anatomical sites for a more detailed collection of electrical energy produced from the body structures. This flexibility of positioning and size matching that is afforded with the curvilinear-shaped sensor electrode 36 are unique features that are not shared with conventional electrode sensors used in typical electrophysiological testing applications.

The high flexibility and conductivity of the curvilinear-shaped electrode sensor 36 of FIGS. 2A-2B is well suited for use in a variety of electrophysiological testing applications. EEG, EOG, EMG, fEMG, ERG, ECG and VEP are only a few examples of electrophysiological testing applications in which the curvilinear-shaped electrode sensor 36 has utility. These electrophysiological testing applications are not meant to limit the application of the curvilinear-shaped electrode sensor 36 or any other of the various embodiments of electrode sensors described herein. It is understood that the flexible, comfortable, soft-form, and simple construction of the curvilinear-shaped electrode sensor 36 as well as the other embodiments of electrode sensors described herein are suitable for use with a variety of electrophysiological testing applications in which it may be desirable to target body structures at a multiple of anatomical sites with a large or enhanced sensing area that can target those structures.

FIGS. 3-8 illustrate a few examples of electrophysiological testing applications in which the curvilinear-shaped electrode sensor 36 of FIGS. 2A-2B is applied to a patient. These examples are only illustrative of a few possible uses of the curvilinear-shaped electrode sensor 36 and are not meant to limit the applicability of this electrode sensor and other sensors described herein. Although not illustrated, it is understood that the various other embodiments of electrode sensors described herein can be placed in use with some of the electrophysiological testing applications depicted in FIGS. 3-8 as well as other applications that have a need for a flexible, comfortable, soft-form, simple construction electrode sensor having a large or enhanced sensing area that can target body structures at a multiple of anatomical sites. For example, one of the electrode sensors described herein could have applicability in use with VEP on patients with alopecia or baldness. In this scenario, the electrode sensors of the various embodiments of the present invention described herein could be placed directly on the dermis at the visual cortex and on the appropriate reference and ground locations.

Figure 3:
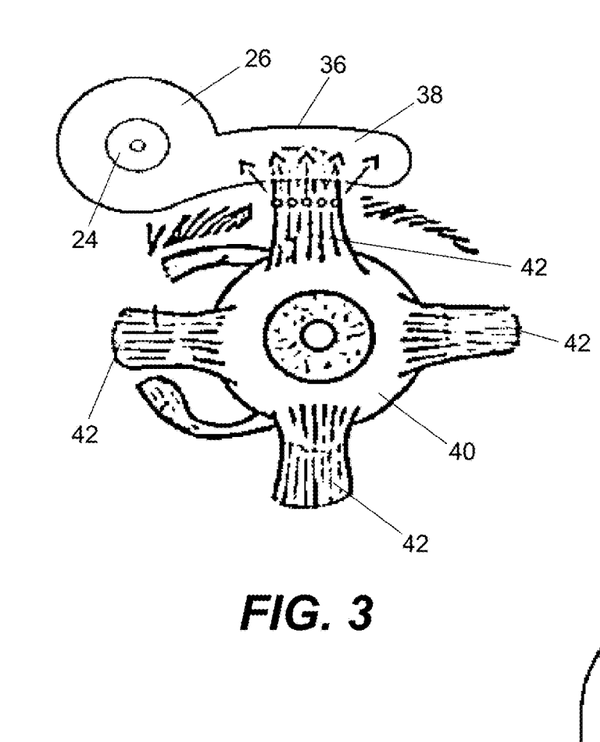
FIG. 3 is a front view of a human eye depicting the extra-ocular muscles with a curvilinear-shaped electrode sensor that is generally equidistant from one of the extra-ocular muscles that is targeted for electrooculography (EOG) testing that can receive radiated energy produced during the testing according to an embodiment.

FIG. 3 shows an example of the curvilinear-shaped electrode sensor 36 used in an EOG testing application. In particular, FIG. 3 illustrates a front view of a human eye 40 depicting one of the extra-ocular muscles 42 with the curvilinear-shaped electrode sensor 36 placed at a generally equidistant location with respect to a targeted extra-ocular muscle 42. In this example, the curvilinear-shaped electrode sensor 36 is placed generally transverse to and equidistant from the superior rectus, which is the extra-ocular muscle targeted for the EOG testing. In this manner, the curvilinear-shaped electrode sensor 36 can receive the radiated electrical energy from the superior rectus that is produced during the testing in response to stimuli applied to the eye 40. The radiated electrical energy, which can range from microvolts to fractions of microvolts, can then be amplified and analyzed by an electrophysiology device or system coupled to the electrode sensor 36 by the connector 24. The electrophysiology device or system can use the timing and amplitude of the superior rectus's electrical signals and compare them against a similar reference area in which the targeted signal is not expected to be found. It is understood that other types of monitoring and diagnoses may be performed on the generated electrical signals. Furthermore, it is understood that the electrode sensor 36 could be applied to any of the other extra-ocular muscles 42 of the eye 40 in a similar fashion.

Figure 4:
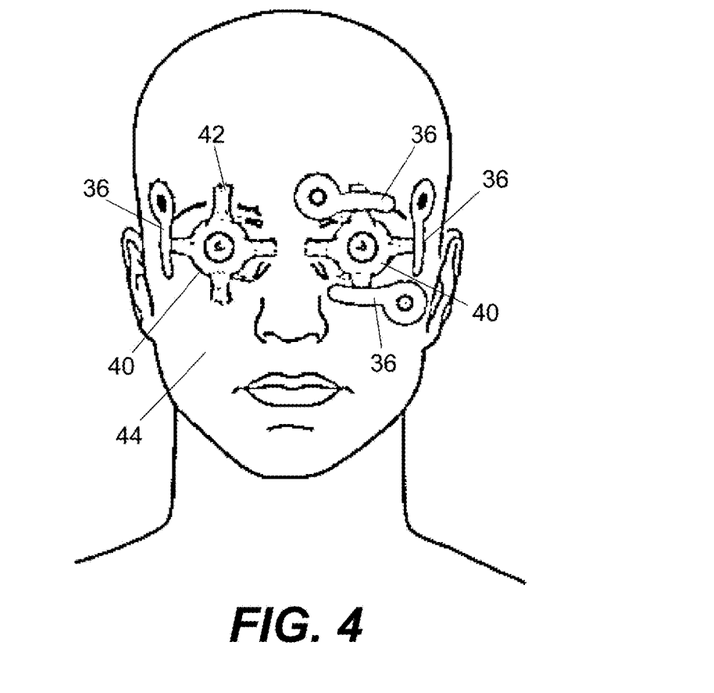
FIG. 4 is a front plan view of a human face showing placement of several curvilinear-shaped electrode sensors at multiple eye adnexa locations for signal sensing for EOG testing according to an embodiment.

FIG. 4 shows an example of curvilinear-shaped electrode sensors 36 used in another EOG testing application. In particular, FIG. 4 illustrates a front plan view of a human face 44 showing placement of several curvilinear-shaped electrode sensors 36 at multiple eye adnexa locations for signal sensing during EOG testing according to an embodiment. In this example, the left eye 40 has curvilinear-shaped electrode sensors 36 placed at generally equidistant locations from several extra-ocular muscles 42. More specifically, the curvilinear-shaped electrodes 36 are placed at generally equidistant locations from the superior rectus, the lateral rectus, and the inferior rectus of the left-eye, while the right-eye 40 has a curvilinear-shaped electrode 36 placed at a generally equidistant location from the lateral rectus.

In this example, the curvilinear-shaped electrode sensors 36 placed about the various extra-ocular muscles 42 of the right and left eyes 40 can receive the radiated electrical energy from these muscles, and an electrophysiology device or system can use the electrical signals for monitoring and assessing the function or dysfunction of the various extra-ocular muscles. It is understood that other configurations of the electrode sensors 36 with the extra-ocular muscles 42 of the right and left eyes 40 are possible and that the illustration depicted in FIG. 4 is not meant to limit the various embodiments of the present invention described herein.

Figure 5:
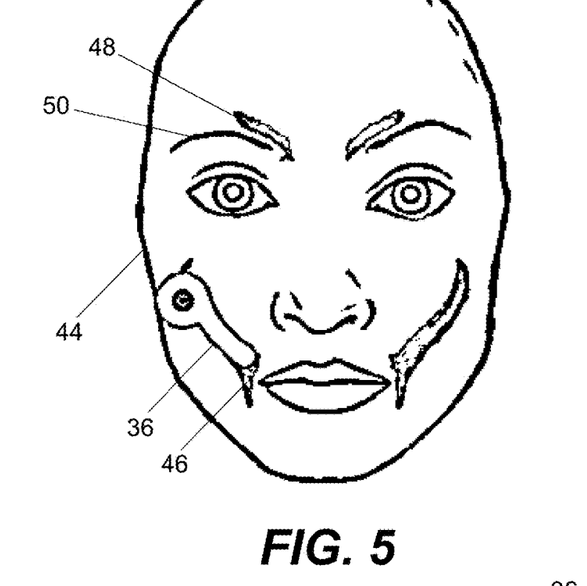
FIG. 5 is a front plan view of a human face showing placement of a curvilinear-shaped electrode sensor over the Zygomaticus major muscle for facial electromyography (fEMG) testing according to an embodiment.

FIG. 5 shows an example of the curvilinear-shaped electrode sensor 36 used in a fEMG testing application. In particular, FIG. 5 illustrates a front plan view of a human face 44 showing placement of a curvilinear-shaped electrode sensor 36 over the Zygomaticus major muscle 46 on the right side of the face for fEMG testing according to an embodiment. This example demonstrates the capability of the curvilinear-shaped electrode sensor 36 to be directly placed on the dermis of the patient overlying a targeted body structure (e.g., a facial muscle—the Zygomaticus major muscle in this example) such that the electrode sensor substantially matches morphometrically with the targeted muscle(s). In a fEMG test of the Zygomaticus major muscle 46 in this example, the curvilinear-shaped electrode sensor 36 can receive the radiated electrical energy from this muscle, and an electrophysiology device or system can use the electrical signals to measure the muscle activity by detecting and amplifying the electrical signals that are generated by the Zygomaticus muscle fibers 46 when they contract in response to a stimulus.

Figure 6:
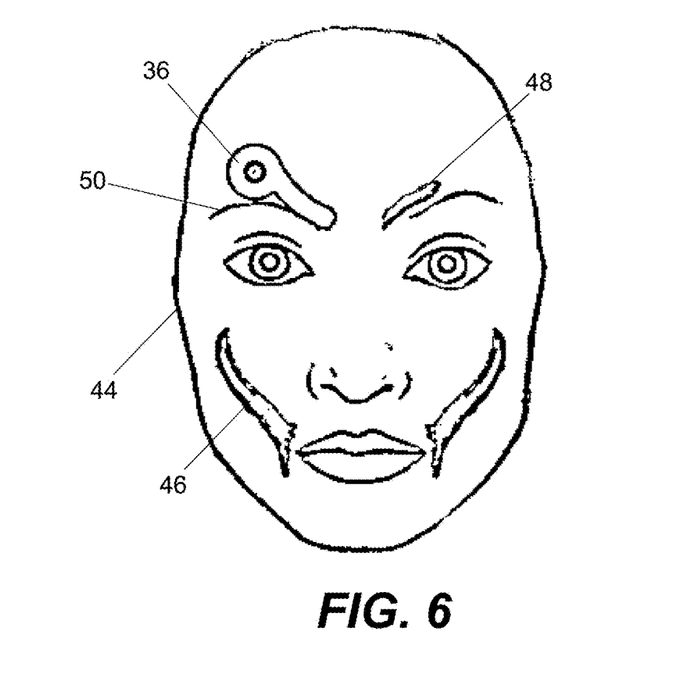
FIG. 6 is a front plan view of a human face showing placement of a curvilinear-shaped electrode sensor over the corrugator supercili muscle for fEMG testing according to an embodiment.

Those skilled in the art will appreciate that there are additional configurations in which the electrode sensor 36 can be used in a fEMG test of the face 44 other than the one illustrated in FIG. 5 and is not meant to limit the various embodiments of the present invention described herein. For example, FIG. 6 shows a curvilinear-shaped electrode sensor 36 placed over the corrugator supercili muscle 48 located near the eye brows 50 that are associated with frowning. In this embodiment, the curvilinear-shaped electrode sensor 36 can be directly placed on the dermis of the patient overlying the corrugator supercili muscle 48 such that the electrode sensor substantially matches morphometrically with this muscle.

It is understood that the illustrations of FIGS. 5-6 are only examples of possible uses of the electrode sensor 36 on the face 44 for a fEMG test and are not meant to limit the various embodiments of the present invention described herein. For example, more than one electrode sensor 36 could be used to target the Zygomaticus major muscle 46 and the corrugator supercili muscle 48. Furthermore, it is understood that the fEMG test could be used to target other muscles in the face 44 than those depicted in FIGS. 5-6.

Figure 7:
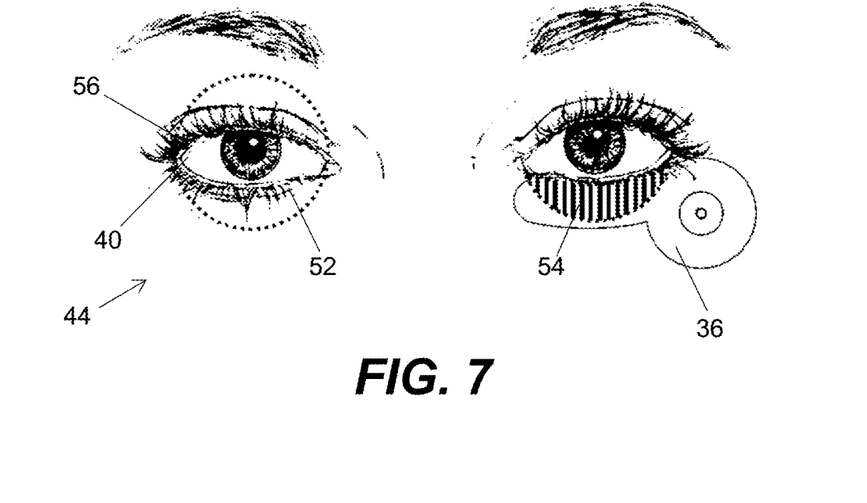
FIG. 7 is a front plan view of a human face showing placement of a curvilinear-shaped electrode sensor over the lower lid to attain large coverage of the smile-shaped retina-adjacent area, bounded generally by the typical 24 mm diameter of the human eye, for electroretinography (ERG) testing according to an embodiment.

FIG. 7 shows an example of the curvilinear-shaped electrode sensor 36 used in an ERG testing application. In particular, FIG. 7 is a front plan view of a human face 44 showing placement of a curvilinear-shaped electrode 36 over the lower lid 52 of an eye 40 to attain large coverage of the smile-shaped lid area overlying the retina 54 which is generally bounded by the scleral circumference of a typical 24 mm diameter of the human eye. In this example illustrated in FIG. 7, the curvilinear-shaped electrode 36 complements the size, location and morphology of the lower lid 52. In particular, the width of the sensing area of the curvilinear-shaped electrode 36 closely matches (e.g., within +/−20%) a total horizontal dimension of a typical human eye 40 and the human retina. As a result, the large sensing area of the curvilinear-shaped electrode 36 that is maximized for coverage will generally match morphometrically with the smile-shaped retinal area 54 underlying the upper lid 56 or the lower lid 52.

This is in contradistinction with conventional electrode sensors used in ERG tests that utilize a small "substantially square" or "substantially round" typically metallic spot for the sensing area. These substantially square sensing areas used with the conventional electrode sensors approximately match an average size of the human pupil (approximately 35 $mm^2$), and have a narrow application area due to its small size. In particular, these small conventional electrode sensors used in ERG are typically defined to be applied "inline and below the pupil of the eye", and target structures that are generally not morphometrically substantially square and cover only a small fraction of the underlying smile-shaped targeted tissue. As mentioned herein, medical professionals are needed for placement of these small substantially square or round electrodes at this location below the pupil. Placement of these conventional electrode sensors is not a trivial matter for these professionals. As a result, some of these conventional electrode sensors require a visual indicator integrated with the sensor to aid the professional in placing it below the pupil. The large sensing area of the curvilinear-shaped electrode 36 with respect to the total surface area of the sensor obviates the need for a high precision alignment of the sensing area in relation to targeted structures, which in this example, is defined to be below the pupil for sensing retinal energy.

Figure 8:
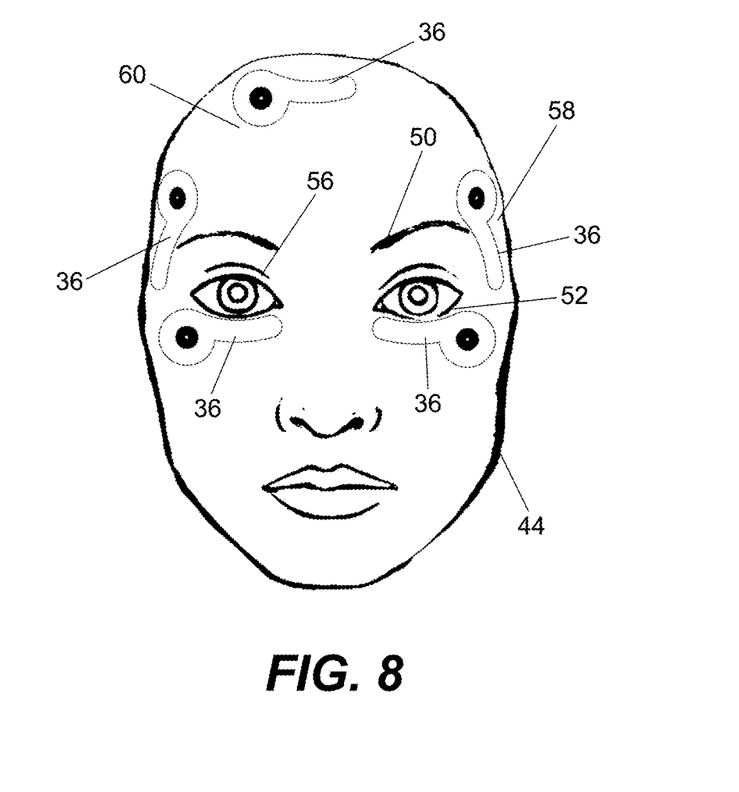
FIG. 8 is a front plan view of a human face showing placement of curvilinear-shaped electrode sensors over a variety of locations including lower eyelids for active signals, temples for reference signals, and forehead for ground for ERG testing according to an embodiment.

FIG. 8 shows an example of the curvilinear-shaped electrode sensor 36 used in another ERG testing application according to an embodiment. In particular, FIG. 8 illustrates a front plan view of a human face 44 showing placement of curvilinear-shaped electrodes 36 over a variety of locations including lower eyelids 52 for active signals, the temples 58 for reference signals, and the forehead 60 for ground in an ERG test.

In this example, these curvilinear-shaped electrode sensors 36 provide substantial coverage of the various body structures situated near the anatomical sites in which they are placed on the face 44. The curvilinear-shaped electrode sensors 36 placed on the lower eyelids 52 act as the signal sensors for the ERG test, while the electrode sensors 36 placed about the temples 58 and the forehead 60 serve as additional reference and ground sensors, respectively. In this manner, these electrode sensors 36 can receive the radiated electrical energy from their respective targeted body structures and convert the electrical energy to electrical signals representative of the radiated electrical energy, which an electrophysiology device or system can use for monitoring and assessing the function or dysfunction of the eyes 40 of the patient. It is understood that there are other configurations in which the electrode sensors 36 can be placed for an ERG test other than that depicted in FIG. 8, and thus, this implementation of the sensors is not meant to limit the various embodiments of the present invention described herein.

As described herein, the electrode sensors of the various embodiments described herein can be modifiable to a targeted size or shape that is tailored to the patient or certain body structure of the patient that is subject of an electrophysiological testing application. The thin and highly flexible nature of the electrode sensors described herein make them modifiable to obtaining a size and shape that is targeted specifically for a certain patient that has body structures that differ from the norm. This allows the electrode sensors described herein to be customized for a fitting to individual facial features or targeted physiology of the patient.

Figure 9:
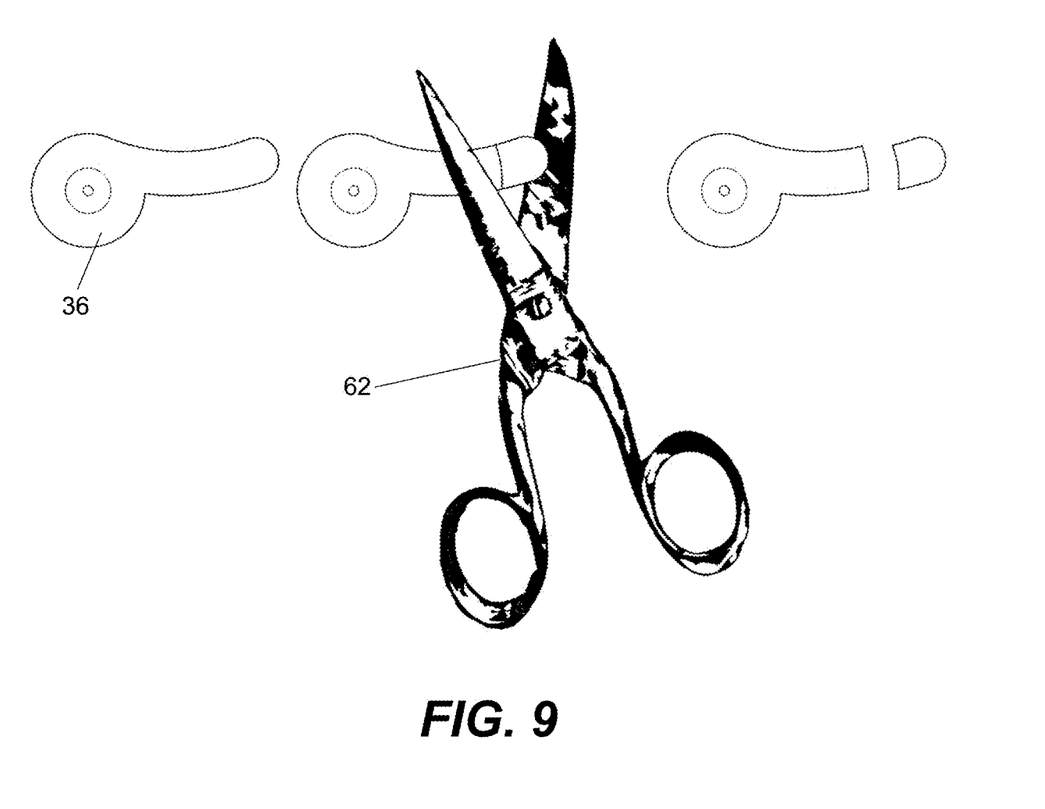
FIG. 9 illustrates an example of alteration or modification of the sensing area of a curvilinear-shaped electrode sensor to a targeted sensing area geometry according to an embodiment.

FIG. 9 illustrates an example of an alteration or modification of the sensing area of a curvilinear-shaped electrode sensor 36 to a targeted sensing area geometry according to an embodiment. In this example, the curvilinear-shaped electrode 36 can be modified by trimming the conductive film area of the electrode sensor, e.g., by using a pair of scissors 62. The trimming of the curvilinear-shaped electrode sensor 36 will not affect operation of its sensing area since the conductive film that forms its sensing area is continuous throughout, and thus, the amount of the sensing area that remains after trimming presumably can be configured to match morphometrically with the body structure that the electrode sensor 36 has been specifically tailored for by making the modification. As noted above, the aspect of having an electrode sensor that is modifiable to obtain a customized fit that is tailored to the individual facial features, body structures, or targeted physiology of a patient is an advantage over common disposable electrodes that customarily have a sensing area constrained to a non-modifiable hard metal or other conductive material surrounded by a non-conductive film or cloth carrier.

It is understood that the electrode sensors described herein can be cut or trimmed in a number of different ways and the modification thereof is not meant to be limited to the use of the scissors 62. For example, a knife, a scalpel or other common sharps can be used to cut the electrode sensor. As described herein, in one embodiment, the electrode sensors can be prefabricated with one or more score lines and/or visual indications to facilitate cutting the sensors at predetermined locations. Each of these score lines and/or visual indications can be representative of a size that is expected to fit different patients of different sizes and shapes.

Figure 10:
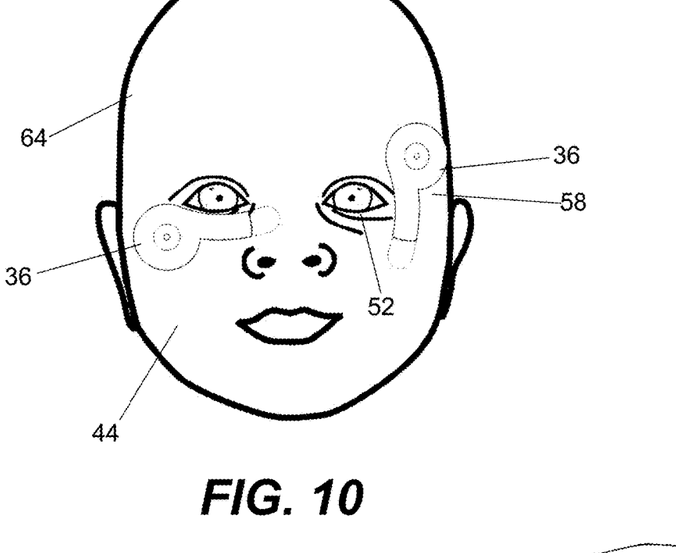
FIG. 10 is a front plan view of a human infant face showing curvilinear-shaped electrodes that have been modified in size and placed on the right lower eyelid for signal sensing for ERG testing and on the left temple for left lateral rectus monitoring for EOG testing according to an embodiment.

FIG. 10 illustrates an example in which curvilinear-shaped electrodes 36 have been modified in size and placed on the face 44 of an infant or a small child 64. In particular, FIG. 10 shows a front plan view of the face 44 of the infant 64 having curvilinear-shaped electrodes 36 that have been modified in size and placed on the right lower eyelid 52 for signal sensing for ERG testing and on the left temple 58 for left lateral rectus monitoring for EOG testing. It is understood that other facial, head and eye features of the infant 64 may utilize curvilinear-shaped electrodes 36 that are modified to more closely match the body structures of the infant, and that examples illustrated in FIG. 10 are not meant to limit the possible features and body structures of an infant or other patients that may have a need for electrode sensors that have been tailored to complement those features and body structures.

The soft-form geometry of the electrode sensors described herein are not limited to curvilinear shapes. Instead, the electrode sensors of the present invention can include a number of different shaped geometries. The selection of the shape of the geometry can depend on the size and shape of the individual features, body structures, or particular physiology that is to be targeted for a specific electrophysiological test. An electrode sensor with whatever soft-form geometry is selected can be flexible and comfortable and have a simple construction that has a large, enhanced or maximized sensing area that can target body structures at a multiple of anatomical sites of a patient undergoing medical-type monitoring and/or diagnosis.

In one embodiment, the electrode sensor can include a rectangular-shaped geometry. In this embodiment, the electrode sensor can include a mono-layer of conductive film having a first side adapted for placement facing an anatomical site of a patient and a second side, opposing the first side, which can be adapted to connect with an electrophysiological device. The conductive film can be shaped with a generally rectangular geometry that is pre-configured and/or modifiable to conform to a targeted shape that is tailored to the patient. The targeted shape can include having at least one edge of the rectangular geometry having either a single edge curve and/or a concave curved edge. The conductive film can include a sensing area that substantially matches morphometrically with a body structure of the patient that is proximate the anatomical site in which the electrode sensor is applied. In this manner, the sensing area can collect electrical signal representations of electrophysiological electrical energy generated from the body structure upon electrical stimulation and generate signal representations thereof.

The rectangular-shaped electrode sensor can further include a connector coupled to the conductive film. The connector can include a base portion formed on the first side and the second side of the conductive film and a projection element supported by the base portion that extends outward through the second side of the conductive film. This connector can take the form of an offset connector, however, it is understood that other types of connectors are suitable for use with this rectangular-shaped electrode sensor.

The rectangular-shaped electrode sensor can further include a non-conductive material formed on only a portion the first side of the conductive film and a hydrogel coated over the first side of the conductive film and the non-conductive material. The materials for the non-conductive material as well as the various types of hydrogels described herein are also suitable for use with the rectangular-shaped electrode sensor.

Figure 11:
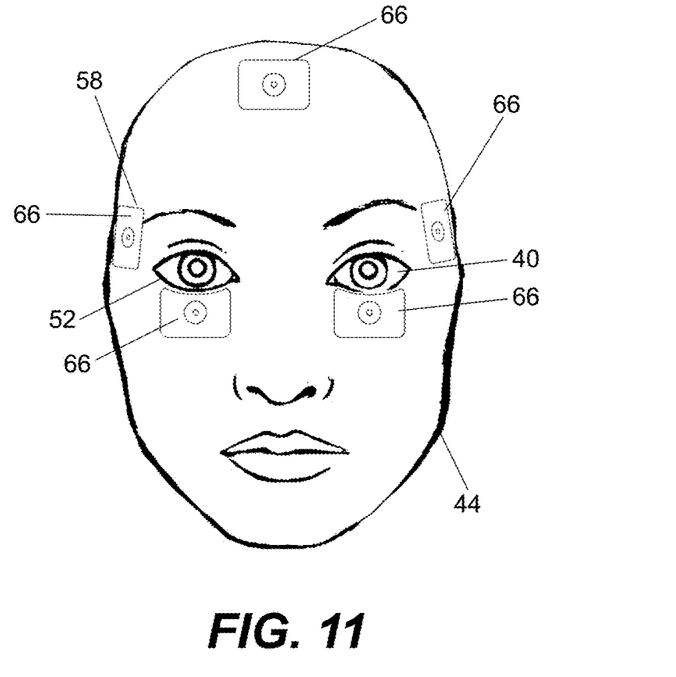
FIG. 11 is a front plan view of a human face showing placement of alternative electrode sensors with the structure depicted in FIG. 1 in a rectangular shape, with some of the sensors having a curved edge for fitment at eyelid locations and some of the sensors without curved edges for reference and ground locations for ERG testing according to an embodiment.

FIG. 11 illustrates an example of various rectangular-shaped electrode sensors 66 that include the aforementioned structure in an electrophysiological testing application according to an embodiment of the present invention. FIG. 11 also shows examples of some rectangular-shaped electrode sensors having at least one edge that includes a single edge curve and/or a concave curved edge. In the example of FIG. 11, the rectangular-shaped electrode sensors 66 having a curved edge are placed at lower eyelid 52 locations, while some of the rectangular-shaped sensors without curved edges are placed at the temples 58 and the forehead 60 of the patient. In this manner, the rectangular-shaped electrode sensors 66 having the curved edge placed at the lower eyelid 52 locations are for active signals, while the rectangular-shaped sensors without curved edges placed at the temples 58 and the forehead 60 are for reference signals and ground, respectively, for an ERG test.

Like the embodiment depicted in FIG. 8 in which curvilinear-shaped electrode sensors are used in an ERG test, the rectangular-shaped electrode sensors 66 of FIG. 11 provide substantial coverage of the various body structures situated near the anatomical sites in which they are placed on the face 44. The rectangular-shaped electrode sensors 66 placed on the lower eyelids 52, the temples 58 and the forehead 60 can receive the radiated electrical energy from their respective targeted body structures. An electrophysiology device or system can use the electrical signals for real-time monitoring and/or diagnosis of the health of the eye 40 of the patient. It is understood that there are other configurations in which the rectangular-shaped electrode sensors 66 can be placed for an ERG test than that depicted in FIG. 11, and thus, this configuration of the sensors is not meant to limit the various embodiments of the present invention described herein.

Those skilled in the art will appreciate that the various electrode sensors described herein can have various other features that enhance the viability of the sensors with a number of electrophysiological testing applications. For example, the electrode sensors of the various embodiments can include a covering or a shield placed over the sensing area on the air-exposed side for shielding and/or labeling purposes. Another feature can include packaging for the electrode sensors. For example, the electrode sensors can be placed in an airtight pouch to retard any dehydration of the bio-compatible hydrogel surfaces (e.g., an Ag/AgCl). In one embodiment, the electrode sensors can be affixed as pairs or multiples to a semi-rigid polyester release plate for protection of the very flexible sensors. In this manner, any air exposed surfaces to the hydrogel will be minimized.

Figure 12:
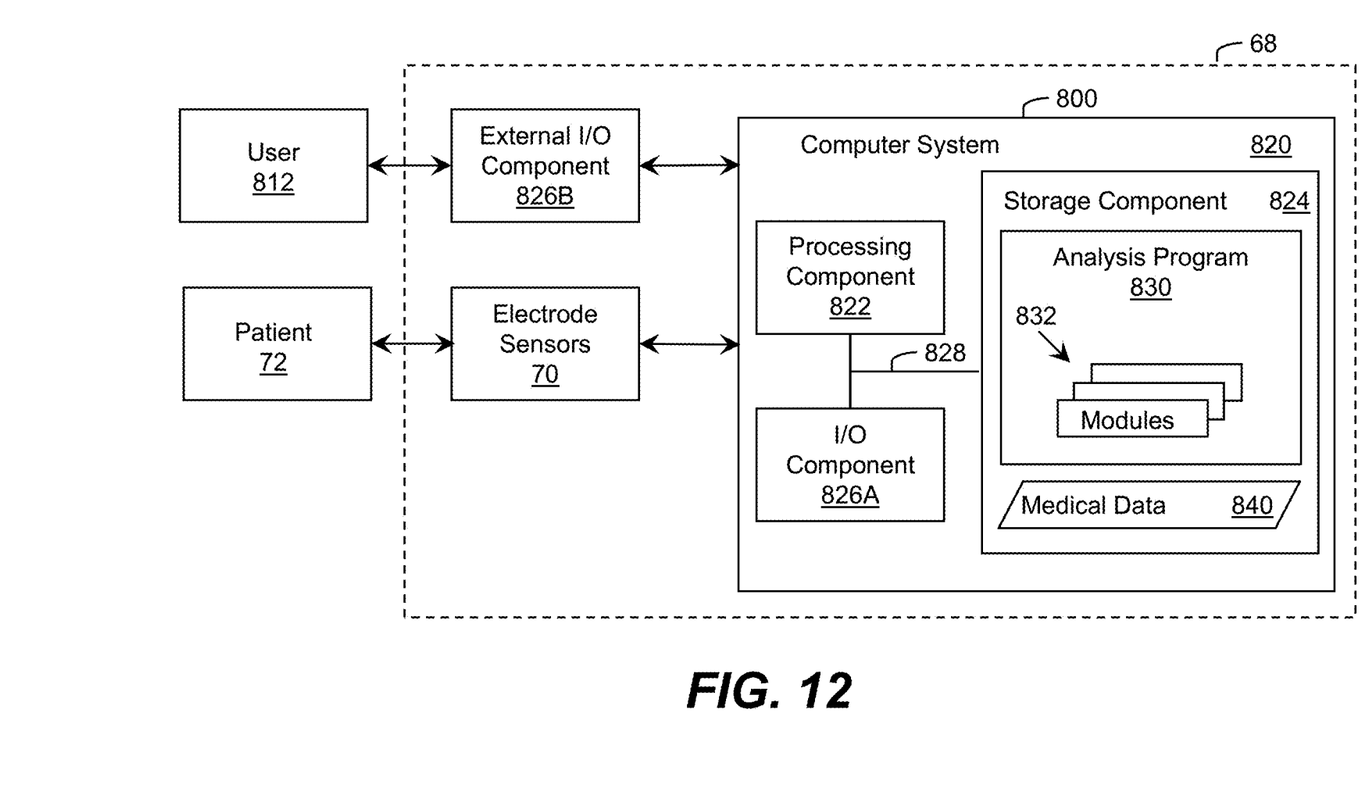
FIG. 12 shows a schematic of an electrophysiological testing system that can include using the curvilinear-shaped electrodes and/or rectangular-shaped electrodes described herein according to an embodiment.

FIG. 12 shows a schematic of an electrophysiological testing system 68 that can include using the electrode sensors described herein, such as the curvilinear-shaped electrodes and/or rectangular-shaped electrodes, according to an embodiment. In this embodiment, the electrophysiological testing system 68 can include any computer-based electrophysiological testing system or device that uses electrode sensors to monitor and/or diagnose a patient in real-time. The electrode sensors described herein, such as the curvilinear-shaped electrodes and/or rectangular-shaped electrodes, are depicted in FIG. 12 as reference element 70. For the purposes of illustrating the interaction of some of the components of the electrophysiological testing system 68, the electrode sensors 70 are illustrated as part of the testing system 68, however, it is understood that the sensors can be separate elements that work in conjunction with and at the direction of various components that form the electrophysiological testing system 68.

As depicted in FIG. 12, the electrophysiological testing system 68 can include a control unit 800. In one embodiment, the control unit 800 can be implemented as a computer system 820 including an analysis program 830, which makes the computer system 820 operable to manage operation of the electrophysiological test system 68, including collection of signals corresponding to the electrical energy sensed by the sensors 70 and any signal processing performed on the signals representative of the electrical energy. In particular, the analysis program 830 can enable the computer system 820 to operate the electrophysiological test system 68 including collecting the signal data generated by the sensors 70 and processing data corresponding to one or more attributes pertaining to a patient 72 on whom the sensors are applied, which can be acquired by the sensors 70, and/or a historical data stored as medical data 840. The computer system 820 can use the medical data 840 to control one or more aspects of the electrophysiological test applied to the patient 72.

Furthermore, one or more aspects of the electrophysiological test can be controlled or adjusted by a user 812, such as a medical professional via an external interface input/output component 826B. The external interface input/output component 826B can be located on the exterior of the electrophysiological testing system 68. The external interface input/output component 826B can include a touch screen that can selectively display user interface controls, such as control dials, which can enable the user 812 to adjust one or more attributes, parameters associated with the electrophysiological test. In an embodiment, the external interface input/output component 826B could conceivably include a keyboard, a plurality of buttons, a joystick-like control mechanism, and/or the like, which can enable the user 812 to control one or more aspects of the operation of the electrophysiological testing system 68. However, it is understood that the external input/output component 826B also can comprise a component which enables interaction with a user 812, which may be physically located remote from the patient 72.

The computer system 820 is shown including a processing component 822 (e.g., one or more processors, signal processing unit), a storage component 824 (e.g., a storage hierarchy), an input/output (I/O) component 826A (e.g., one or more I/O interfaces and/or devices), and a communications pathway 828. In general, the processing component 822 executes program code, such as the analysis program 830, which is at least partially fixed in the storage component 824. While executing program code, the processing component 822 can process data, which can result in reading and/or writing transformed data from/to the storage component 824 and/or the I/O component 826A for further processing. The pathway 828 provides a communications link between each of the components in the computer system 820. The I/O component 826A and/or the external interface I/O component 826B can comprise one or more human I/O devices, which enable a human user 812 to interact with the computer system 820 and/or one or more communications devices to enable a system user 812 to communicate with the computer system 820 using any type of communications link. To this extent, during execution by the computer system 820, the analysis program 830 can manage a set of interfaces (e.g., graphical user interface(s), application program interface, and/or the like) that enable human and/or system users 812 to interact with the analysis program 830. Furthermore, the analysis program 830 can manage (e.g., store, retrieve, create, manipulate, organize, present, etc.) the data, such as medical data 840, using any solution. As used herein, unless otherwise noted, the term "set" means one or more (i.e., at least one) and the phrase "any solution" means any now known or later developed solution.

In any event, the computer system 820 can comprise one or more general purpose computing articles of manufacture (e.g., computing devices) capable of executing program code, such as the analysis program 830, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 830 can be embodied as any combination of system software and/or application software.

Furthermore, the analysis program 830 can be implemented using a set of modules 832. In this case, a module 832 can enable the computer system 820 to perform a set of tasks used by the analysis program 830, and can be separately developed and/or implemented apart from other portions of the analysis program 830. When the computer system 820 comprises multiple computing devices, each computing device can have only a portion of the analysis program 830 fixed thereon (e.g., one or more modules 832). However, it is understood that the computer system 820 and the analysis program 830 are only representative of various possible equivalent monitoring and/or control systems that may perform a process described herein with regard to the control unit. To this extent, in other embodiments, the functionality provided by the computer system 820 and the analysis program 830 can be at least partially be implemented by one or more computing devices that include any combination of general and/or specific purpose hardware with or without program code. In each embodiment, the hardware and program code, if included, can be created using standard engineering and programming techniques, respectively.

Regardless, when the computer system 820 includes multiple computing devices, the computing devices can communicate over any type of communications link. Furthermore, while performing a process described herein, the computer system 820 can communicate with one or more other computer systems, such as the user 812, using any type of communications link. In either case, the communications link can comprise any combination of various types of wired and/or wireless links; comprise any combination of one or more types of networks; and/or utilize any combination of various types of transmission techniques and protocols.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An electrode sensor, comprising:
a mono-layer of conductive film, the conductive film having a first side adapted for placement facing an anatomical site of a patient and a second side, opposing the first side, having direct exposure to an ambient environment of the patient, wherein a size and shape of the conductive film define an entire size and shape of the electrode sensor in a plan view, wherein the conductive film includes a sensing area that is modifiable to a targeted size and defined by at least one concave curved outer edge of the conductive film configured to be complementary to a morphology of a body structure of the patient that is proximate the anatomical site, the sensing area adapted to collect electrical signal representations of electrophysiological electrical energy generated from the body structure and generate signal representations thereof; and
a connector coupled to the conductive film for connection to an electrophysiological device; a non-conductive material located adjacent to only a portion of the first side of the conductive film, wherein the non-conductive material extends along the first side of the conductive film beyond a perimeter of the connector, with one end of the non-conductive material being in vertical alignment with a first end of the conductive film and another opposing end of the non-conductive material extending along the first side of the conductive film to a mid-region thereof, wherein the non-conductive material overlays the connector and only the first side of the conductive film extending from the first end to beyond the perimeter of the connector to the mid-region.

2. The electrode sensor of claim 1, wherein the conductive film includes a carbon conductive film impregnated with a silver conductive treatment.

3. The electrode sensor of claim 2, wherein the silver conductive treatment includes Ag/AgCl.

4. The electrode sensor of claim 1, wherein the connector includes a base portion formed on the conductive film and a projection element supported by the base portion that extends outward through the conductive film and the base portion.

5. The electrode sensor of claim 1, further comprising a bio-compatible hydrogel coated over the first side of the conductive film and the non-conductive material, wherein the non-conductive material separates the hydrogel from direct contact with the connector.

6. The electrode sensor of claim 5, wherein the bio-compatible hydrogel comprises an Ag/AgCl hydrogel.

7. The electrode sensor of claim 1, wherein the sensing area of the conductive film is modifiable to the targeted size by trimming a portion thereof.

8. The electrode sensor of claim 1, wherein the conductive film is shaped with a soft-form geometry including a curvilinear shape.

9. The electrode sensor of claim 1, wherein the first side of the conductive film further includes a non-sensing area outside of the sensing area, and wherein the connector is surrounded by the non-sensing area, offset from the sensing area.

10. An electrode sensor, comprising:
- a mono-layer of conductive film that is continuously conductive from a first end to an opposing second end, the conductive film having a first side adapted for placement facing an anatomical site of a patient and a second side, opposing the first side, the conductive film including a large sensing area located proximate to the second end and shaped with a curvilinear geometry that is modifiable to a targeted size, wherein a size and shape of the conductive film defines an entire size and shape of the electrode sensor in a plan view, wherein the large sensing area is partially defined by a concave curved outer edge of the conductive film, a convex curved outer edge of the conductive film parallel to the concave curved outer edge, and a rounded second end of the conductive film, and wherein the large sensing area is adapted to collect electrical signal representations of electrophysiological electrical energy generated from a body structure of the patient and generate signal representations thereof;
- a connector coupled to the conductive film proximate the first end, wherein the connector includes a base portion formed on the first side and the second side of the conductive film and a projection element supported by the base portion that extends outward through the second side of the conductive film;
- a non-conductive material located adjacent to only a portion of the first side of the conductive film, wherein the non-conductive material extends along the first side of the conductive film beyond a perimeter of the connector to define a non-sensing area of the conductive film; and
- a hydrogel coated over the first side of the conductive film and the non-conductive material, wherein the non-conductive material separates the hydrogel from direct contact with the connector.

11. The electrode sensor of claim 10, wherein the conductive film includes a carbon conductive film impregnated with a silver conductive treatment, wherein the silver conductive treatment includes Ag/AgCl.

12. The electrode sensor of claim 10, wherein the hydrogel comprises Ag/AgCl.

13. The electrode sensor of claim 10, wherein the large sensing area is complementary to a size and morphology of a tissue or organ, located on a face, head, or an eye of the patient, and wherein the conductive film is a carbon conductive film having a thickness up to about 5 mils.

14. The electrode sensor of claim 10, wherein the large sensing area of the conductive film provides at least partial circumference coverage of the body structure.

15. The electrode sensor of claim 10, wherein the large sensing area provides complete coverage of the size, the location and the morphology of the body structure.

16. The electrode sensor of claim 10, wherein the large sensing area encompasses about 25% to about 50% of a total surface area occupied by the conductive film and the connector.

17. The electrode sensor of claim 10, wherein the non-sensing area has an elliptical shape.

18. An electrode sensor for detecting electrophysiological electrical energy generated from an anatomical site of a patient, comprising:
- a mono-layer of conductive film having a first side adapted for placement facing the anatomical site of the patient and a second side, opposing the first side, having direct exposure to an ambient environment of the patient at least in a sensing area of the conductive film, wherein the conductive film is a carbon conductive film having a thickness up to about 5 mils and a size and shape of the conductive film define an entire size and shape of the electrode sensor in a plan view, the conductive film shaped with a rounded rectangular geometry that is modifiable to a targeted shape that is tailored to the patient, the sensing area adapted to collect electrical signal representations of electrophysiological electrical energy generated from a body structure located on a face, head, or an eye of the patient and generate signal representations thereof;
- a connector coupled to the conductive film, wherein the connector includes a base portion formed on the first side and the second side of the conductive film and a projection element supported by the base portion that extends outward through the second side of the conductive film;
- a non-conductive material overlaying only a portion of the first side of the conductive film corresponding to the connector, wherein the non-conductive material defines a non-sensing area of the conductive film; and
- a hydrogel coated over the first side of the conductive film and the non-conductive material, wherein the non-conductive material separates the hydrogel from direct contact with the connector.

19. The electrode sensor of claim 18, wherein the conductive film includes a carbon conductive film impregnated with a silver conductive treatment.

20. The electrode sensor of claim 18, wherein the hydrogel comprises Ag/AgCl.

* * * * *